United States Patent [19]

Yamazaki et al.

[11] Patent Number: 4,566,319
[45] Date of Patent: Jan. 28, 1986

[54] PROCESS AND APPARATUS FOR MEASURING THERMAL SHRINKAGE PROPERTIES OF YARN

[75] Inventors: Chikayasu Yamazaki; Jun Torikai, both of Otsu; Ichiro Kumo, Shiga, all of Japan

[73] Assignee: Toray Industries, Inc., Tokyo, Japan

[21] Appl. No.: 483,431

[22] Filed: Apr. 8, 1983

[30] Foreign Application Priority Data

Apr. 9, 1982 [JP] Japan .................................. 57-58022

[51] Int. Cl.⁴ ............................................ G01N 33/36
[52] U.S. Cl. ...................................... 73/160; 28/219; 28/281; 73/862.48
[58] Field of Search ...................... 73/160, 829, 862.48; 57/264, 265; 374/49, 50; 28/248, 281, 241, 246, 219

[56] References Cited

U.S. PATENT DOCUMENTS

| | | | |
|---|---|---|---|
| 2,385,894 | 10/1945 | Taylor | 28/246 |
| 3,726,137 | 4/1973 | Denton | 73/160 |
| 3,762,220 | 10/1973 | Gusack et al. | 73/160 |
| 4,295,252 | 10/1981 | Robinson et al. | 73/160 |
| 4,295,360 | 10/1981 | Fountain | 73/160 |
| 4,347,993 | 9/1982 | Leonard | 318/6 |
| 4,393,701 | 7/1983 | Lawson | 73/160 |
| 4,393,725 | 7/1983 | Satterfield | 73/160 |

FOREIGN PATENT DOCUMENTS

| | | | |
|---|---|---|---|
| 94220 | 7/1975 | Japan | 28/246 |
| 155161 | 12/1981 | Japan | 73/862.48 |
| 883874 | 12/1961 | United Kingdom | 73/160 |
| 672229 | 7/1979 | U.S.S.R. | 28/246 |

OTHER PUBLICATIONS

"Crimp Characterization Instrument," Research Disclosure, Apr. 1974, pp. 48-50.

Primary Examiner—Stewart J. Levy
Assistant Examiner—JOhn E. Chapman, Jr.
Attorney, Agent, or Firm—Austin R. Miller

[57] ABSTRACT

The thermal shrinkage properties of yarn are measured by applying heat treatment to the yarn while it travels through a straight yarn path formed between a feed roller and a draw roller. The peripheral speed of the feed roller is set at a desired constant peripheral speed $V_1$. The tension T of the yarn is detected at the downstream of the feed roller, and the peripheral speed of the draw roller is controlled at a speed $V_2$ so that the detected tension T becomes equal to a desired preset tension $T_0$ of the yarn. The thermal shrinkage $S(\%)$ is measured through the computation of $S=[(V_1-V_2)/V_1]\times 100$. If the controlling of the peripheral speed $V_2$ of the draw roller is effected so that $V_2/V_1=$a desired constant value, the detected tension of the yarn can be used for measuring the thermal shrinkage stress of the measured yarn.

23 Claims, 7 Drawing Figures

PROCESS AND APPARATUS FOR MEASURING THERMAL SHRINKAGE PROPERTIES OF YARN

BACKGROUND OF THE INVENTION

1. Field of the Invention

The present invention relates generally to measurement of the thermal shrinkage properties of yarn, more particularly to a process and apparatus for measuring the thermal shrinkage properties such as the thermal shrinkage or the thermal shrinkage stress of yarn, especially, thin or fine yarn less than 300 denier. The measuring process and apparatus may be applied to various kinds of yarn, such as fully drawn yarn, undrawn yarn, partially oriented yarn, textured yarn, spun yarn and fancy yarn of synthetic and natural yarn.

2. Description of the Prior Art

A typical process and apparatus for measuring the thermal shrinkage properties of yarn, for example, the thermal crimp of a textured yarn upon being subjected to hot water, is disclosed in U.S. Pat. No. 3,762,220 granted to Gusack et al.

In the measurement, yarn is caused to travel from a drive roll to a pulley, passing through a idler pulley. The idler pulley is disposed in a hot water bath positioned below the level of the drive roll and pulleys. That is, the yarn travels in a V-shaped path. The drive roll is driven at a constant peripheral speed $V_1$, and the pulley is driven via a magnetic coupling. When the yarn travels through the hot water bath, thermal crimp of the yarn is generated. Therefore, the peripheral speed of the pulley is reduced so as to absorb the thermal crimp of the yarn. Consequently, the thermal crimp $C(\%)$ of the yarn is determined by evaluating the equation of $C=[(V_1-V_2)/V_1]\times 100$, where $V_2$ is the peripheral speed of the pulley.

The conventional measuring process and apparatus, however, is inaccurate when applied to the measurement of the thermal shrinkage or the thermal shrinkage stress of thin or fine yarn. This is because while the yarn travels along the periphery of the idler pulley, it is subjected to large contact friction, which causes a difference in yarn tension between the positions before and after the idler pulley. This difference is increased by the friction in the bearing of the idler pulley.

This difference in yarn tension can be ignored in the measurement of the thermal shrinkage or thermal shrinkage stress of thick yarn, since the thermal stress of thick yarn is extremely large. However, if the yarn is less than 300 denier, particularly less than 100 denier, the thermal stress is very small. In such cases, the above-mentioned difference in yarn tension before and after the idler pulley results in an error in measurement that cannot be ignored. Further, since the difference in yarn tension before and after the idler pulley is changeable, the conventional measuring process and apparatus lack reproducibility.

SUMMARY OF THE INVENTION

An object of the present invention is to eliminate the above-mentioned defects of the conventional process and apparatus for measuring the thermal shrinkage properties of yarn.

Another object of the present invention is to provide a process for accurate measurement of thermal shrinkage properties of yarn, such as the thermal shrinkage and the thermal shrinkage stress of yarn.

A further object of the present invention is to provide an apparatus for carrying out the above-mentioned process.

In accordance with one aspect of the present invention, there is provided a process for measuring the thermal shrinkage properties of yarn. The process comprises the steps of traveling a yarn through a substantially straight yarn path formed between a feed roller maintained at a desired constant peripheral speed $V_1$ and a draw roller; applying heat treatment to the traveling yarn between the feed roller and the draw roller so that the traveling yarn generates thermal shrinkage; detecting tension of the traveling yarn downstream of the feed roller; driving the draw roller at a peripheral speed $V_2$ so that the detected tension T of the traveling yarn becomes equal to a desired constant tension $T_0$; and obtaining the thermal shrinkage $S(\%)$ of the traveling yarn by the equation of $S=[(V_1-V_2)/V_1]\times 100$.

For carrying out the above process, there is provided an apparatus which comprises a pair of feed roller and draw roller arranged to be horizontally spaced from each other so that a substantially straight yarn path is formed between these rollers; a first controller for driving the feed roller at a desired constant peripheral speed $V_1$; a heat treatment unit for applying the thermal shrinkage to the traveling yarn, the unit being disposed between the feed roller and the draw roller; a tensiometer for detecting a tension T of the traveling yarn, the tensiometer being disposed between the feed roller and the draw roller; a second controller for driving the draw roller at a peripheral speed $V_2$ so that the detected tension T becomes equal to a desired constant tension $T_0$; and an evaluator for evaluating the thermal shrinkage $S(\%)$ by the equation of $S=[(V_1-V_2)/V_1]\times 100$, the evaluator being connected to both the first and second controllers.

In another aspect of the present invention, there is provided another process for measuring the thermal shrinkage properties of yarn. The process comprises the steps of traveling a yarn through a substantially straight yarn path formed between a feed roller maintained at a desired constant peripheral speed $V_1$ and a draw roller maintained at a desired constant peripheral speed $V_2$; applying heat treatment to the traveling yarn between the feed roller and the draw roller so that the traveling yarn generates thermal shrinkage; and obtaining the thermal shrinkage stress by detecting the tension T of the traveling yarn downstream of the feed roller.

In accordance with a further aspect of the present invention, there is provided an apparatus for carrying out the above-defined process. The apparatus comprises a pair of feed roller and draw roller arranged to be horizontally spaced from each other so that a substantially straight yarn path is formed between these rollers; a first controller for driving the feed roller at a desired constant peripheral speed $V_1$; a heat treatment unit for applying the thermal shrinkage to the traveling yarn, the unit being disposed between the feed roller and the draw roller; a tensiometer for detecting a tension T of the traveling yarn, the tensiometer being disposed between the feed roller and the draw roller; and a second controller for driving the draw roller at a desired constant peripheral speed $V_2$.

DESCRIPTION OF THE PREFERRED EMBODIMENTS

Figure 1:
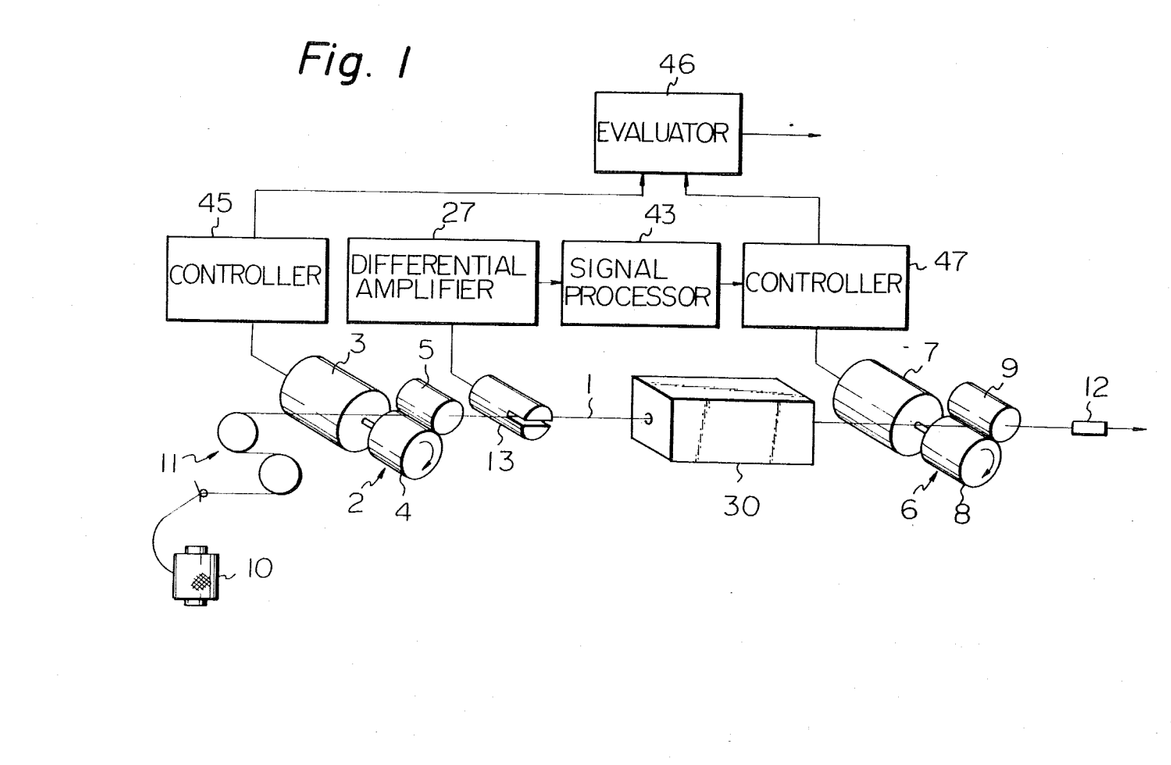
FIG. 1 is a schematic block diagram of an apparatus for a measuring process according to an embodiment of the present invention.

In FIG. 1, a feed roller 2 for a yarn 1 comprises a drive roller 4, driven by a stepping motor 3, and a nip roller 5 in contact with the drive roller 4. A draw roller 6 for the yarn 1 similarly comprises a drive roller 8, driven by a stepping motor 7, and a nip roller 9 in contact with the drive roller 8. The feed roller 2 and the draw roller 6 are horizontally spaced from one another so as to form a substantially straight yarn path.

The yarn 1 is taken from a yarn package 10 and subjected to pretension from a tension regulator 11 arranged between the yarn package 10 and the feed roller 2. The tension regulator 11 consists of a magnetic brake, a dancer roller, or a friction brake and applies to the yarn 1 a pretension of 20 through 200 mg/denier, preferably, 20 through 100 mg/denier. An ejector 12, such as an air ejector, is disposed downstream of the draw roller 6. On the yarn path between the feed and draw rollers 2 and 6, a tensiometer 13 and a heat treatment unit 30 are disposed, each described later.

Figure 2:
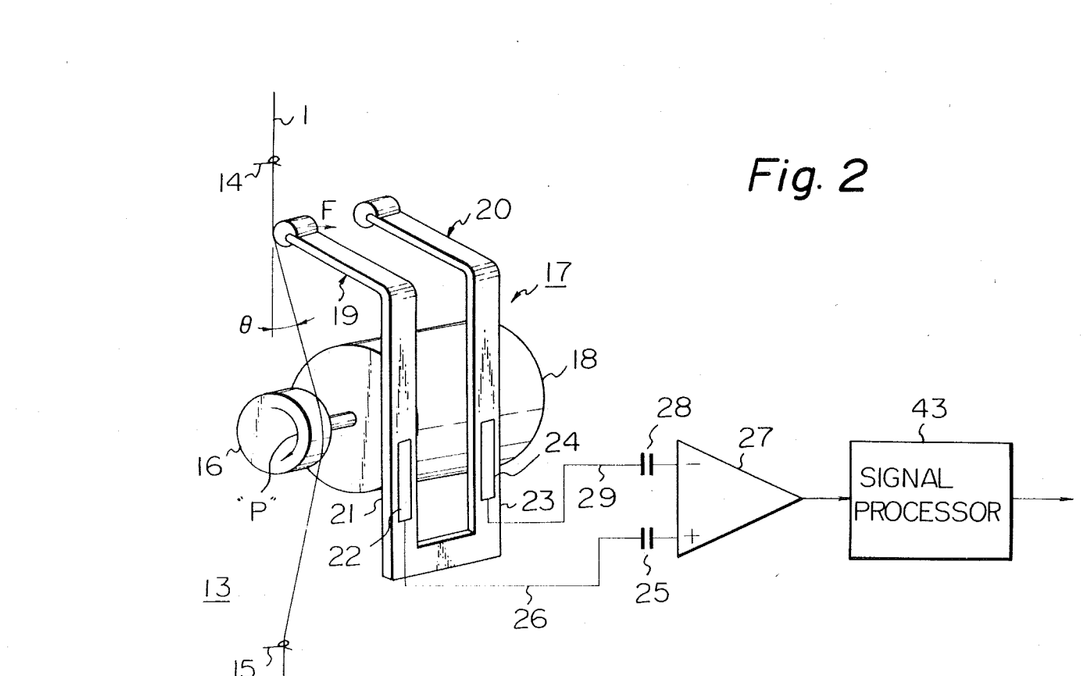
FIG. 2 is a schematic perspective view of an embodiment of a tensiometer employed for the apparatus of FIG. 1.

Referring to FIG. 2, an embodiment of the tensiometer 13 comprises a pair of spaced yarn guides 14 and 15 and, arranged therebetween, an eccentric rotor 16 and a gauge 17. The eccentric rotor 16 is driven by a motor 18 so as to rotate in the same direction as the traveling yarn 1, as shown by an arrow "P" in FIG. 2. The eccentric rotor 16 periodically deflects the yarn 1 traveling between the yarn guides 14 and 15 at an angle of $\theta$ against the straight line connecting the two yarn guides 14 and 15. The deflection angle $\theta$ varies from an angle $\theta_1$ through an angle $\theta_2$ in every rotation of the eccentric rotor 16 under the following conditions: $\theta_1 = 0.5$ through 2.0 degrees, $\theta_2 = 1.0$ through 10 degrees, and $\theta_1 < \theta_2$. The rotational speed of the eccentric rotor 16 is from 20 to 100 times per second, preferably, from 30 to 60 times per second.

The gauge 17 comprises a pair of identical gauges, i.e., a detection gauge 19 for detecting the tension of the yarn traveling between the yarn guides 14 and 15 and a dummy gauge 20 for compensating the vibration of the tensiometer 13. The detection gauge 19 comprises a lever 21 made of a resilient plate, such as a metallic plate, and a semiconductor strain gauge 22 attached to the surface of the lever 21. The dummy gauge 20 comprises a similar resilient lever 23 and semiconductor strain gauge 24 attached to the surface of the lever 23.

The lever 21 of the detection gauge 19 is disposed so that one end is always in contact with the traveling yarn 1. Therefore, the lever 21 always receives at the end thereof a pressing force F from the traveling yarn 1. The pressing force F acting on the lever 21 is proportional to the tension of the traveling yarn 1 and is changed by the semiconductor strain gauge 22 into an electric signal. The electric signal, which is capable of indicating the tension of the yarn 1, is fed to a differential amplifier 27 through a lead wire 26 and an electric capacitor 25. The capacitor 25 allows only the alternating current component of the electric signal detected by the semiconductor strain gauge 22 to pass into the differential amplifier 27.

The dummy gauge 20 is not in contact with the traveling yarn 1. Therefore, the vibration of the lever 23 caused by the vibration of the tensiometer 13 is detected by the semiconductor strain gauge 24 and is fed to the above-mentioned differential amplifier 27 through a lead wire 29 and an electric capacitor 28. The capacitor 28 allows only the alternating current component of an electric signal detected by the semiconductor strain gauge 24 to pass into the differential amplifier 27. Accordingly, any noise component in the signal detected by the detection gauge 19 due to the vibration of the tensiometer 13 is compensated by the differential amplifier 27. That is, the output of the differential amplifier 27 includes no electric noise component.

The output of the differential amplifier 27 is subsequently fed to a signal processor 43 in which the computation of $F_2 - F_1 = T(\sin \theta_2 - \sin \theta_1)$ is carried out, where $F_1$ is the pressing force acting on the lever 21 when the yarn 1 is deflected an angle $\theta_1$ by the eccentric rotor 16, $F_2$ is the pressing force acting on the lever 21 when the yarn 1 is deflected an angle $\theta_2$ by the eccentric rotor 16, and T is the tension of the traveling yarn 1. The output of the signal processor 43 directly indicates the above-mentioned tension T of the traveling yarn 1.

At this stage, it should be understood that since the maximum deflection angle of the yarn 1 is at most 10 degrees, the yarn path is substantially straight between the feed roller 2 (FIG. 1) and the draw roller 6 (FIG. 1).

The above-mentioned tensiometer 13 employing the eccentric rotor 16 is preferred because of the low friction loss of the yarn 1. Alternatively, however, a so-called three-point type tensiometer, which comprises two separate guide rollers for guiding the yarn 1 and a detection roller arranged between the two separate guide rollers so as to deflect the yarn between the two guide rollers, may be employed. The deflection angle of the yarn 1 against the straight line connecting the both guide rollers is at most 15 degrees, preferably, not more than 10 degrees.

Referring again to FIG. 1, a heat treatment unit 30 is arranged between the tensiometer 13 and the draw roller 6. The heat treatment unit 30 heats the traveling yarn 1 without bend for 0.2 through 5 seconds. When the yarn 1 is heated, it shrinks. The heat treatment unit 30 may consist of either a dry heat furnace or a hot water bath.

Figure 3:
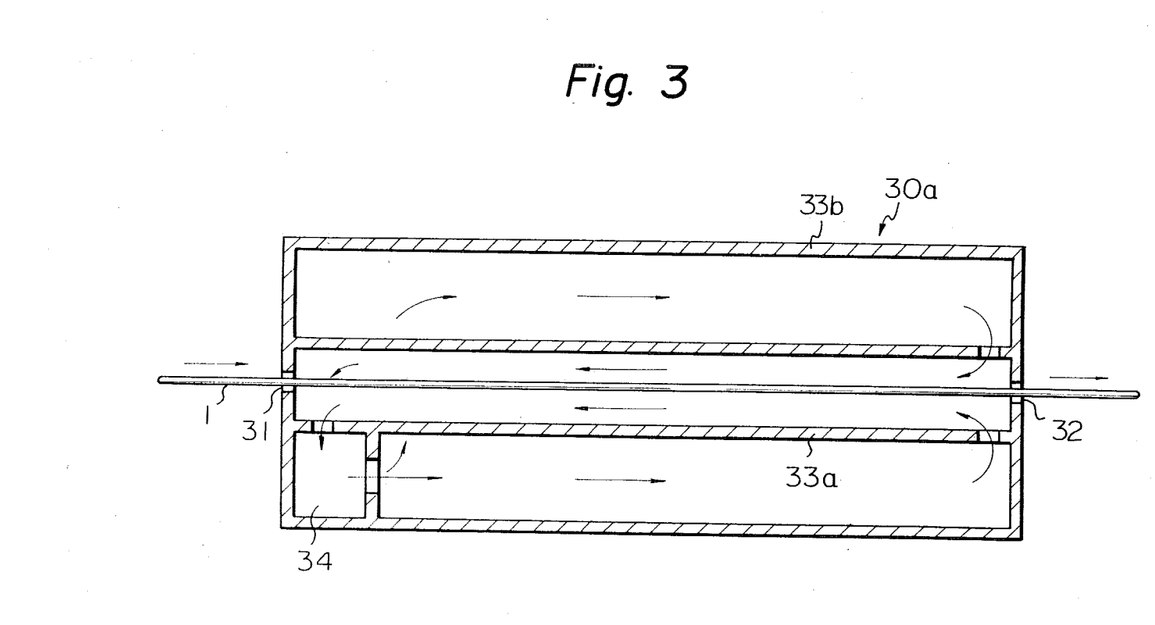
FIG. 3 is a schematic sectional view of a dry heat furnace for the heat treatment of yarn employed for the apparatus of FIG. 1.

FIG. 3 illustrates an embodiment of a dry heat furnace 30a having a double-tube structure. The dry heat furnace 30a comprises an inner tube 33a and an outer tube 33b, a yarn inlet 31 and a yarn outlet 32 provided at opposite ends of the inner tube 33a, and a hot air generator 34 attached to the outer tube 33b. The hot air generator 34 generates hot air maintained at a desired temperature of 80° C. through 250° C. The hot air circulates through the outer tube 33b in the direction shown by arrows and then through the inner tube 33a in the opposite direction against the traveling direction of the yarn 1 and returns to the hot air generator 34.

It should be understood that the counter flow of the hot air is not an indispensable condition for the present invention. That is, the flow of the hot air may also be in the same direction as the traveling direction of the yarn 1. However, to prevent entering of unheated air through the yarn inlet 31 into the inner tube 33a accompanying the traveling yarn 1, the counter flow is preferable. As a result, the temperature distribution within the inner tube 33a becomes more uniform in the lengthwise direction.

Since the dry heat furnace 30a does not wet the yarn 1 during the heat treatment and does not adversely affect the operation of the tensiometer 13 (FIG. 1), the dry heat furnace 30a may alternatively be arranged at a position between the feed roller 2 and the tensiometer 13.

Figure 4:
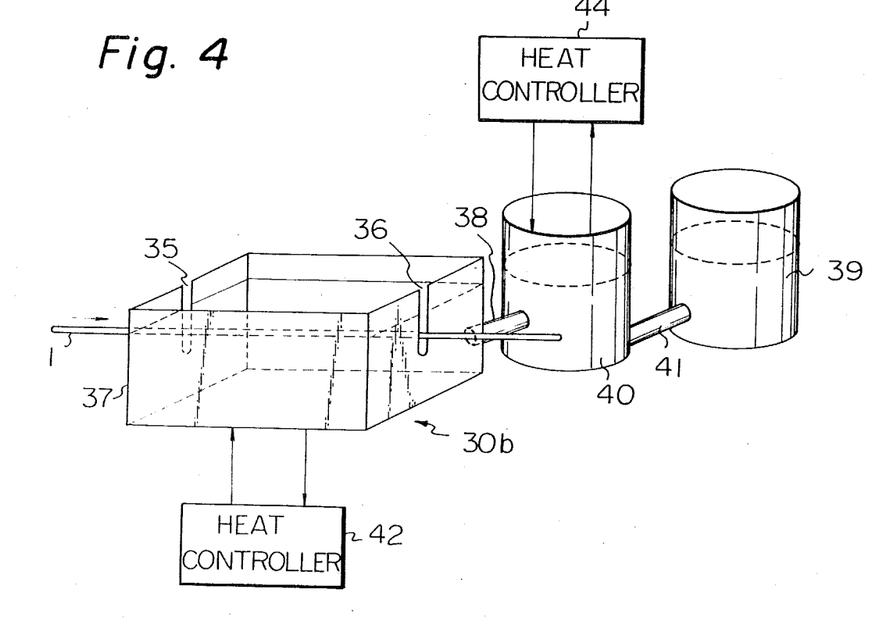
FIG. 4 is a schematic perspective view of an embodiment of a hot water bath for the heat treatment of yarn employed for the apparatus of FIG. 1.

FIG. 4 illustrates an embodiment of a hot water bath 30b for applying to the yarn 1 a hot water treatment. In FIG. 4, the hot water bath 30b comprises a heat bath 37 having U-shaped narrow yarn inlet 35 and outlet 36 at the front and rear faces thereof, a water supply tank 39 for supplying water to the heat bath 37 through a preheating tank 40. The water supply tank 39 is connected to the preheating tank 40 by a conduit 41. The preheating tank 40 is connected to the heat bath 37 by another conduit 38. The water supply tank 39 adopts a overflow mechanism (not shown) so that the water levels of the water supply tank 39, the preheating tank 40, and the heat bath 37 are kept constant.

The yarn inlet 35 and outlet 36 are 0.2 through 2.0 mm wide so as to allow the yarn 1 to travel under the surface of hot water without causing any bend therein and to minimize the leakage of the hot water. The water level of the heat bath 37 is maintained by the surface tension of the hot water.

The hot water in the heat bath 37 is kept at a constant temperature between 60° C. and 100° C. by a heater (not illustrated in FIG. 4) and a heat controller 42. The preheating tank 40 is arranged for compensating for the leakage of the hot water from the heat bath 37. The water supplied from the preheating tank 40 is preheated so as not to cause any appreciable change in the temperature of the hot water within the heat bath 37. Therefore, the water of the preheating tank 40 should preferably be preheated to a suitable temperature within 10° C. not higher than that of the hot water of the heat bath 37. The water of the preheating tank 40 is not preheated to a temperature more than that of the hot water of the heat bath 37. The temperature of the hot water of the preheating tank 40 is controlled constant by a heat controller 44 and a heater (not illustrated). The preheating tank 40 should preferably be provided with a suitable water agitator, such as an air bubbler. At this stage, it should be noted that the preheating tank 40 is not indispensable. In some cases, the heat bath 37 may be directly connected to the water supply tank 39. Further, in case that the yarn 1 is coated with finish or lubricant, a small amount of surface active agent, such as a cationic or anionic surface active agent, is preferably added into the heat bath 37 so that a uniform treatment may be applied to the yarn 1.

With the above-mentioned dry heat furnace 30a and hot water bath 30b, the length between the yarn inlet 31 or 35 and the yarn outlet 32 or 36 is chosen so that the yarn 1 traveling in such furnace 30a or bath 30b is heat-treated for 0.2 to 5.0 seconds. Since the yarn 1 is usually caused to travel at a speed of 1.0 through 100 m/min, preferably, 5 through 60 m/min, the above-mentioned length is 5 through 100 cm, preferably, 10 through 30 cm.

Referring again to FIG. 1, the stepping motor 3 is connected to a controller 45 comprising a conventional electric oscillating circuit, a frequency dividing circuit, and so on for driving the stepping motor 3 and, accordingly, the feed roller 2 is driven at a desired constant peripheral speed of 1.0 through 100 m/min, preferably, 5 through 60 m/min. The controller 45 is also electrically connected to an evaluator 46, such as a computing circuit. The evaluator 46 is also connected to another controller 47 connected to the stepping motor 7 of the draw roller 6. The controller 47 is also connected to the afore-described signal processor 43 of the tensiometer 13. The controller 47 comprises a circuit for presetting a desired constant tension $T_0$ of 1 through 30 mg/denier, preferably 1 through 10 mg/denier, with regard to the yarn 1, a circuit for computing the difference $(T_0-T)$, where T is a tension detected by the tensiometer 13, a circuit for applying a proportional and integral action to the difference $(T_0-T)$, a circuit for converting voltage to frequency, a circuit for driving the stepping motor 7, and so on.

The operation of the apparatus of FIGS. 1 through 4 will now be described.

The yarn 1 taken from the package 10 is set first in the apparatus. At this stage, it should be understood that the yarn 1 of the yarn package 10 usually includes different kinds of yarns connected or knotted in series. Further, a suitable separate roller having a smaller diameter than the drive roller 4 may be arranged to confront the drive roller 4, so that the yarn 1 is wound around the drive roller 4 and the separate roller several turns and is subsequently nipped by the nip roller 5. The arrangement of such separate roller is effective for preventing the slippage of the yarn 1 on the feed roller 2. A similar separate roller may also be arranged in the draw roller 6.

After setting the yarn 1, the feed roller 2 is driven at a desired constant peripheral speed $V_1$ by the stepping motor 3 under the control of the controller 45. The yarn 1 is then wound off from the yarn package 10 and is pretensioned by the tension regulator 11. The yarn 1 is thereafter sent by the feed roller 2 into the heat treatment unit 30, through the tensiometer 13. The yarn 1 is there heated and shrinks and generates the thermal shrinkage stress. The tensiometer 13 detects the tension T of the yarn 1 while the thermal shrinkage stress is generated in the yarn 1 and sends the detected tension T to the controller 47 through the differential amplifier 27 and the signal processor 43. The controller 47 compares the detected tension T with the preset tension $T_0$ and controls the rotation speed of the stepping motor 7 and, accordingly, the peripheral speed of the draw roller 6 is changed so that the relationship of $T=T_0$ is eventually established. For example, if the detected tension T of the yarn 1 is larger than the preset tension $T_0$, the controller 47 controls the rotation speed of the stepping motor 7 so that the peripheral speed of the draw roller 6 is slowed down until the relation of $T=T_0$ is obtained. At this time, the peripheral speed of the draw roller 6 is $V_2$. The evaluator 46 performs the computation of $[(V_1-V_2)/V_1] \times 100$ on the basis of the outputs of both controllers 45 and 47. The result obtained from the computation indicates the thermal shrinkage S(%) of the yarn 1. Moreover, the calibration of the tensiometer 13 is carried out as follows. That is, a yarn with a weight at one end thereof is suspended on the yarn path defined by the two yarn guides 14 and 15. Then, the signal processor 43 is adjusted so that an output corresponding to the weight is obtained.

Apart from the above-mentioned operation, if the draw roller 6 is driven by the stepping motor 7 so that the ratio of the peripheral speed $V_2$ of the draw roller 6 to the peripheral speed $V_1$ of the feed roller 2, i.e., $V_2/V_1$, is 0.7 through 1.8, preferably, 0.9 through 1.2, and if the tension of the yarn 1 is detected by the tensiometer 13, the thermal shrinkage stress (grams) of the yarn 1 is directly obtained from the detected tension T.

From the foregoing description of the operation of the apparatus, it will be understood that the measurement of the thermal shrinkage properties of the yarn 1 can be accomplished even if the apparatus is changed so that the draw roller 6 is rotated at a desired constant peripheral speed while the peripheral speed of the feed roller 2 is adjusted.

In the above-described detection of the tension of the yarn 1 by the tensiometer 13, it is possible to set the minimum deflection angle $\theta_1$ to zero by adjusting the positon of the eccentric rotor 16 (FIG. 2). However, in such case, zero level of the output of the gauge 19 is apt to drift. Therefore, it is necessary to calibrate the zero level frequently. Further, the wave of the output of the gauge 19 will take the shape of the half-wave rectified sinusoidal wave. Accordingly, it is difficult to detect the amplitude of the output. In addition, in this case, since the end of the lever 21 does not always contact the yarn 1, the yarn 1 will periodically tap the end of the lever 21 during the rotation of the eccentric rotor 16. As a result, the deflection of the yarn 1 becomes unstable, and the lever 21 will start to vibrate at its own natural frequency. This fact makes accurate detection of the tension of the yarn 1 difficult. By the reason of the above, the minimum deflection angle $\theta_1$ of the yarn 1 should preferably be adjusted from 0.5 to 2.0 degrees, as described previously. That is, the end of the lever 21 of the gauge 19 is preferably set in contact with the yarn 1 traveling between the yarn guides 14 and 15 (FIG. 2).

Figure 5:
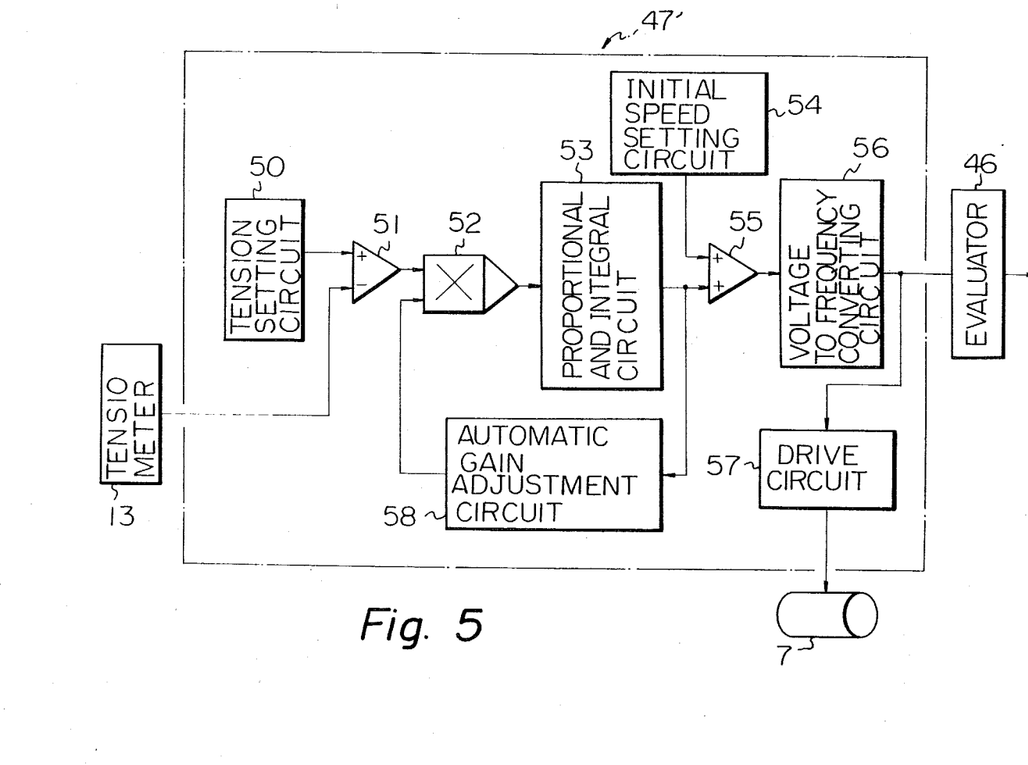
FIG. 5 is a block diagram of an embodiment of a controller of a draw roller employed for the present invention.

By the way, since the yarn 1 is subjected to heat treatment during the measurement of the thermal shrinkage properties and since the yarn 1 usually includes different kinds of yarns having different physical properties, such as a different Young's modulus, it may sometimes be difficult to control the tension of the yarn 1 by controlling the peripheral speed of the draw roller 6. As a result, measurement of the thermal shrinkage properties of the yarn 1 becomes difficult. The controller 47' of FIG. 5 is able to solve the above-mentioned problem. The controller 47' is applied to the apparatus of FIG. 1 by replacing the controller 47 with such controller 47'.

Referring to FIG. 5 in association with FIG. 1, the controller 47' comprises a circuit 50 for setting a desired tension $T_0$ of the yarn 1, a circuit 51 for computing the difference between the preset tension $T_0$ and the detected tension T of the yarn 1 detected by the tensiometer 13, i.e., $T_0-T$, a circuit 52 for multiplying the difference with a control gain G, a circuit 53 for applying a proportional and integral action on the output of the multiplying circuit 52, a circuit 54 for setting an initial peripheral speed $V_0$ of the draw roller 6 so as to be equal to the peripheral speed $V_1$ of the feed roller 2, a circuit 55 for adding the output $\Delta V$ of the proportional and integral circuit 53 and the above-mentioned initial peripheral speed $V_0$, a circuit 56 for converting the output voltage of the adding circuit 55 to a frequency, a circuit 57 for driving the stepping motor 7 in accordance with the output of the voltage to frequency converting circuit 56, and a circuit 58 for automatically adjusting the control gain G in direct proportion of the output $\Delta V$ of the proportional and integral circuit 53. At this stage, the proportional and integral circuit 53 can be, for example, one that is disclosed in as feedback network 69 described in U.S. Pat. No. 4,347,993. The automatic gain adjusting circuit 58 comprises a negative half-wave rectifier circuit, a variable gain inverting amplifier, an adder, and so on.

The operation of the apparatus employing the controller 47' of FIG. 5 will now be described in reference to FIGS. 1 and 5.

The yarn 1 taken from the package 10 is set in the apparatus. Thereafter, the stepping motor 3 is driven by the controller 45 so that feed roller 2 is rotated at a constant peripheral speed $V_1$. The yarn 1 which was wound off from the yarn package 10 is pretensioned by the tension regulator 11 and is then sent to the heat treatment unit 30 through the tensiometer 13. The yarn 1 is thus heated by the heat treatment unit 30 and generates the thermal shrinkage stress. At this time, the tension T of the yarn 1 is detected by the tensiometer 13, and the detected tension T is sent into the controller 47'. The controller 47' compares the detected tension T with the preset tension $T_0$ set in the controller 47' and controls the rotation speed of the stepping motor 7 so that the detected tension T becomes equal to the preset tension $T_0$. As a result, the peripheral speed of the draw roller 6 is regulated. For example, if the detected tension T of the yarn 1 is larger than the preset tension $T_0$, the controller 47' decreases the rotation speed of the stepping motor 7, thereby decreasing the peripheral speed of the draw roller 6. The evaluator 46 computes the equation of $S=[(V_1-V_2)/V_1]\times 100$ on the basis of the peripheral speed $V_1$ of the feed roller 2 and the peripheral speed $V_2$ of the draw roller 6. The result indicates the thermal shrinkage S(%) of the yarn 1. At this time, the automatic gain adjustment circuit 58 of the controller 47' regulates the control gain G so as to be in direct proportion to the afore-mentioned output $\Delta V$ of the proportional and integral circuit 53. The relationship between the output $\Delta V$ and the control gain G is established as follows.

If $\Delta V \leq 0$, $G=\alpha+\beta.|\Delta V|/V_0$, and if $\Delta V>0$, $G=\alpha$. That is to say, if the sign of $\Delta V$ is positive, then $\Delta V$ is changed to zero by the negative half-wave rectifier circuit of the automatic gain adjustment circuit 58, but is kept as it is if the sign thereof is negative. The output $\Delta V$ is then amplified $-\beta/V_0$ times by the variable gain inverting amplifier. Therefore, it becomes zero if $\Delta V$ is positive, while it becomes $+\beta.|\Delta V|/V_0$ if $\Delta V$ is negative. Subsequently, the output zero or $+\beta.|\Delta V|/V_0$ of the variable gain inverting amplifier is added to $\alpha$ by the adder. As a result, the control gain G is defined finally as shown in the above-mentioned two equations. In the two equations, $\alpha$ and $\beta$ are constants determined by experiments in response to the values of the physical properties and the thickness of the yarn 1, the feed speed, the distance between the feed and draw roller, and the preset tension of the yarn. Thus, it is determined that $0<\alpha<0.2$ and $1<\beta<20$, and preferably, $0.02<\alpha<0.06$ and $2<\beta<10$.

From the foregoing, it should be understood that if the yarn 1 shrinks, i.e., if $\Delta V<0$, the control gain G should be increased in accordance with the thermal shrinkage of the yarn 1. That is to say, the more the yarn 1 shrinks, the more the control gain is increased. Thus, in spite of the change in the physical property or properties of the yarn 1 lengthwise thereof, accurate measurement of the thermal shrinkage properties of the yarn is achieved.

In the measurement of the shrinkage stress of the yarn 1 by using the controller 47', the connection between the proportional and integral circuit 53 and the adding circuit 55 is cut off, and the peripheral speed $V_2$ of the draw roller 6 is set by the initial speed setting circuit 54.

The two examples of the test measurement conducted by the measuring process and apparatus of the present invention are described hereinbelow.

EXAMPLE I

The test measurement of the hot water shrinkage of a yarn was conducted by using the apparatus of FIG. 1, 2, 4, and 5. The yarn used for the test measurement was a partially oriented polyester yarn having a thickness of 75 denier, produced by Toray Industries, Inc.

Prior to the test measurement, the specified yarn was formed into two separate packages by the use of two types of surface drive winders at a winding speed of 2700 m/min. At that time, one of the winders was operated under an ordinary condition so that a uniform package having a cylindrical shape is obtained, while the other winder was operated under an abnormal condition so that a package having a saddle-like shape is finally obtained.

Thereafter, the measurement of the thermal shrinkage was conducted on both yarns of the packages, the former being referred to as a normal yarn and the latter being referred to as an abnormal yarn hereinafter. The measuring conditions were as follows.
(1) Peripheral speed of feed roller: 10 m/min
(2) Pretension applied to yarn: 100 mg/denier
(3) Length of heat treatment unit: 17 cm
(4) Hot water temperature: 80° C.
(5) Heating time of yarn: 1.0 second
(6) Preset tension: 5 mg/denier
(7) Rotation speed of eccentric rotor: 45 times/second
(8) Distance between feed and draw rollers: 0.7 m The result of the measurement conducted is illustrated in FIG. 6.

Figure 6:
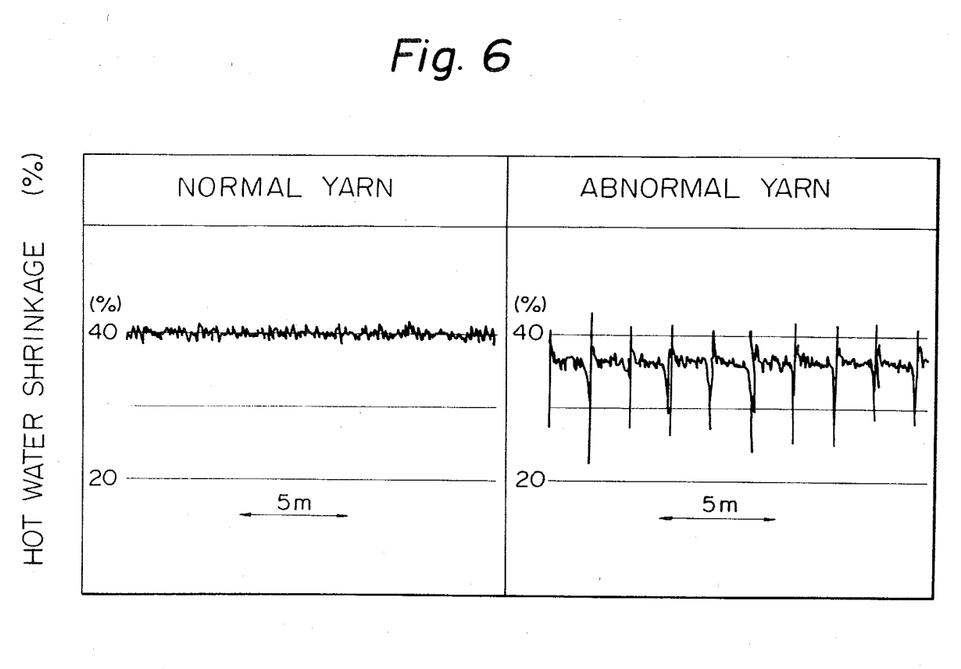
FIG. 6 is a graph of the results of an example measurement conducted by the present invention.

From FIG. 6, it is understood that the hot water shrinkage of the normal yarn was almost constant. However, the hot water shrinkage of the abnormal yarn periodically varied. The varied portions correspond to the yarn which was wound on the ends of the package. With the normal yarn, the polymer consisting of the yarn is in the amorphous state. Therefore, the normal yarn was apt to shrink. On the other hand, since the abnormal yarn was heated by friction at the ends of the package while forming the package, the polymer consisting of the abnormal yarn was partially crystallized. Consequently, the hot water shrinkage of the abnormal yarn varied more than the case of the normal yarn, as indicated in the graphs of FIG. 6. From the test measurement, it is understood that the present invention is very effective for measuring an extremely small amount of variation of physical properties of the yarn.

In the Example I above, the heating temperature of the yarn was set at 80° C. This was because the glass transition point of the used yarn is approximately 80° C. That is, the shrinkage is zero (%) if the heating temperature is below 80° C. and suddenly becomes about 40(%) if the heating temperature is above 80° C. Further, the crystallized portions of the yarn due to the friction have a glass transition point higher than the above-mentioned point. Accordingly, if the heating temperature is set to a temperature between the glass transition point of the normal yarn and that of the abnormal yarn, the difference between the normal and abnormal yarns can be definitely observed since the normal yarn portions shrinks and the abnormal yarn portions do not shrink.

EXAMPLE II

The dry heat shrinkage of the yarn was measured by a partially oriented polyester yarn, produced by Toray Industries Inc.

Prior to the measurement, the yarn was textured by a DF-9 friction type false twister manufactured by Toray Engineering Inc. At that time, 19 different textured yarns were made as test samples by varying the temperature of the heat setting and the texturing speed. The samples of the textured yarns were connected in series for each texturing speed in the order of low to high temperatures of the heat setting. Each yarn was 20 m long. Further, such connected yarns were further connected in series in the order of low to high texturing speed. At both ends of the connected yarns, leading yarns of 20 m long were connected, and subjected to the measurement under the following condition. The measurement was carried out by using the apparatus of FIGS. 1, 2, 3, and 5.
(1) Peripheral speed of yarn feed roller: 10 m/min
(2) Pretension applied to measured yarn: 100 mg/denier
(3) Length of heat treatment unit: 17 cm
(4) Hot air temperature: 130° C.
(5) Heating time of measured yarn: 1 second
(6) Preset tension: 5 mg/denier
(7) Rotation speed of eccentric rotor: 45 times/second
(8) Distance between feed and draw rollers: 0.7 m The result of the measurement was plotted in the graph of FIG. 7. In the graph, the abscissa indicates the temperature of the heat setting for the formation of the measured textured yarn, and the ordinate indicates the dry heat shrinkage.

Figure 7:
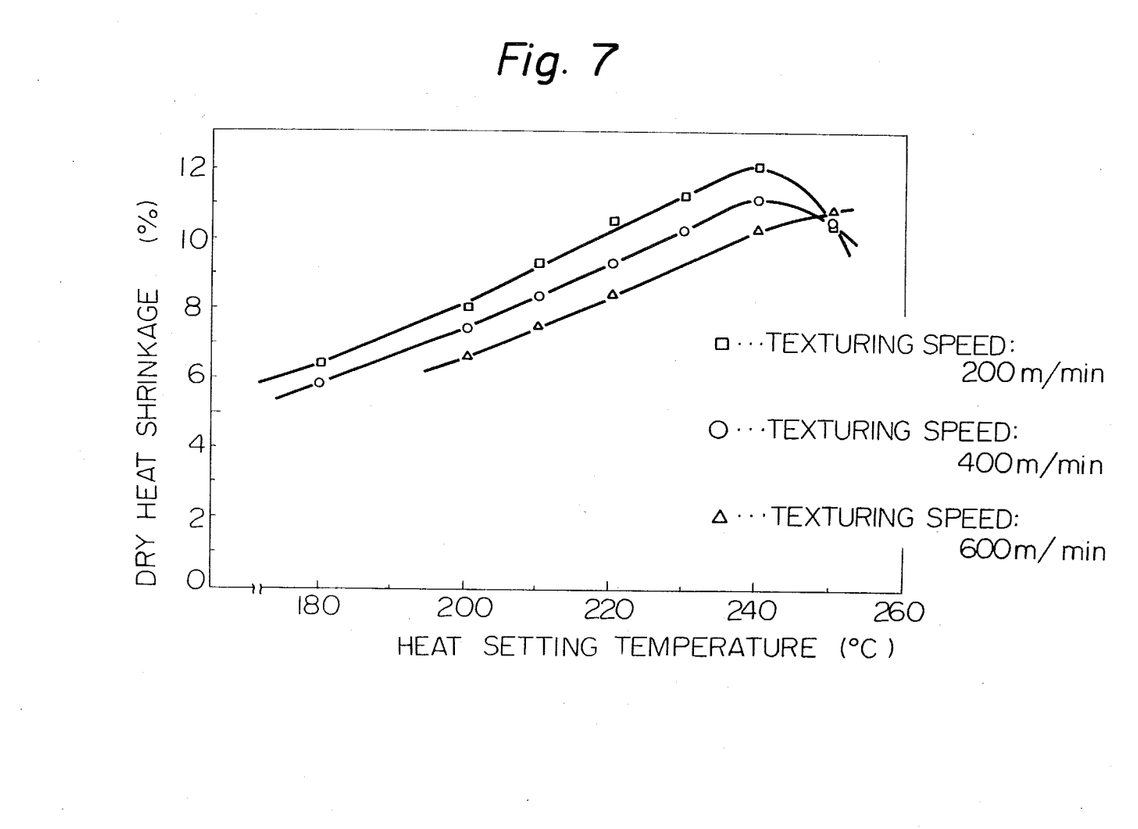
FIG. 7 is a graph of the results of another example measurement conducted by the present invention.

From the graph, it is understood that the dry heat shrinkage clearly shows the texturing condition. That is, according to the present invention, the bulkiness of textured yarns can reliably be determined since the bulkiness corresponds to the texturing conditions.

We claim:
1. A process for measuring thermal shrinkage properties of yarn, which comprises the steps of:
traveling a yarn through a substantially straight and horizontal yarn path between a feed roller maintained at a desired constant peripheral speed $V_1$ and a draw roller;
applying heat treatment to the traveling substantially straight yarn during straight yarn travel along said path between the feed roller and the draw roller by contacting said straight traveling yarn with hot water so that the traveling yarn thermally shrinks;
detecting tension of the straight traveling yarn downstream of the feed roller;
driving the draw roller at a peripheral speed $V_2$ by obtaining the difference of the desired constant tension $T_0$ minus the detected tension $T$, subjecting the difference to a proportional and integral circuit, driving the draw roller in response to an output of the proportional and integral circuit and regulating a control gain of the proportional and integral circuit in proportion to the output thereof so that the detected tension T of the traveling yarn becomes equal to a desired constant tension $T_0$; and obtaining the thermal shrinkage S(%) of the traveling yarn by the equation of $S=[(V_1-V_2)/V_1]\times 100$.

2. The process according to claim 1, wherein the desired contstant tension $T_0$ is from 1 to 30 mg/denier.

3. The process according to claim 2, wherein the desired constant tension $T_0$ is from 1 to 10 mg/denier.

4. The process according to claim 1, wherein the yarn is selected from the group consisting of a fully drawn yarn, an undrawn yarn, a partially oriented yarn, a textured yarn, a spun yarn, or a fancy yarn of synthetic yarn.

5. The process acording to claim 1, wherein a thickness of the yarn is no greater than 300 denier.

6. The process according to claim 5, wherein the thickness of the yarn is no greater than 100 denier.

7. The process according to claim 1, wherein the peripheral speed $V_1$ of the feed roller is from 1 to 100 m/min.

8. The process according to claim 7, wherein the peripheral speed $V_1$ of the feed roller is from 5 to 60 m/min.

9. The process according to claim 1, wherein the heat treatment is applied for 0.2 to 5 sec.

10. The process according to claim 1, further comprising the step of applying pretension to the yarn upstream of the feed roller.

11. The process according to claim 10, wherein the pretension is from 20 to 200 mg/denier.

12. The process according to claim 11, wherein the pretension is from 20 to 100 mg/denier.

13. The process according to claim 1 wherein temperature of the water is from 60° C. to 100° C.

14. An apparatus for measuring the thermal shrinkage properties of traveling yarn comprising:

a feed roller and draw roller pair horizontally spaced from each other so that a substantially straight yarn path is formed between these rollers;

a first controller for driving the feed roller at a desired constant peripheral speed $V_1$;

a heat treatment unit for applying hot water to the horizontally traveling straight yarn to induce thermal shrinkage thereof, between the feed roller and the draw roller;

a tensiometer for detecting a tension T of the horizontally traveling straight yarn, without substantial bending thereof between the feed roller and the draw roller a second controller for driving the draw roller at a peripheral speed $V_2$, the second controller being connected to the tensiometer and comprising an electric circuit for obtaining the differential signal $(T_0-T)$, a proportional and integral circuit for processing the differential signal, a drive circuit for driving the draw roller at the peripheral speed $V_2$ in response to an output of the proportional and integral circuit so that the detected tension T of the traveling yarn becomes equal to the desired constant tension $T_0$ and an electric circiut for regulating a control gain of the proportional and integral circuit in proportion to the output thereof; and an evaluator for evaluating the thermal shrinkage S(%) by the equation of $S=[(V_1-V_2)/V_1]\times 100$, the evaluator being connected to both the first and second controllers.

15. The apparatus according to claim 14, wherein the tensiometer comprises a pair of yarn guides disposed to be spaced from each other for guiding the traveling yarn, an eccentric rotor disposed between the pair of yarn guides for periodically deviating the traveling yarn, and a gauge disposed between the pair of yarn guides for electrically detecting the tension of the traveling yarn.

16. The apparatus according to claim 15, wherein the eccentric rotor always contacts the traveling yarn.

17. The apparatus according to claim 16, wherein the deviation angle of the traveling yarn is 0.5 to 2 degrees in minimum and 1.0 to 10 degrees in maximum based on the straight line connecting the pair of yarn guides.

18. The apparatus according to claim 15, wherein the rotation speed of the eccentric rotor is from 20 to 100 times per second.

19. The apparatus according to claim 18, wherein the rotation speed of the eccentric rotor is from 30 to 60 times per second.

20. The apparatus according to claim 15, wherein the eccentric rotor rotates the same direction as the traveling direction of the yarn.

21. The apparatus according to claim 15, wherein the gauge comprises a detection gauge and a dummy gauge having the same vibration characteristics as the detection gauge.

22. The apparatus according to claim 14, wherein the heat treatment unit includes a preheat tank providing said hot water to said yarn by a conduit and a water supply tank connected to the preheating tank by a conduit.

23. Apparatus according to claim 14 wherein the heat treatment unit includes a hot water bath for circumferentially enveloping said travelling yarn as the yarn travels therethrough, of sufficient thermal mass to substantially instantaneously heat said yarn to the temperature of the water throughout the yarn cross-section upon the yarn entering the bath.

* * * * *